(12) United States Patent
Pulido-Cejudo

(10) Patent No.: US 6,649,743 B1
(45) Date of Patent: Nov. 18, 2003

(54) MONOCLONAL ANTIBODY AGAINST ESTROGEN STIMULATED LEUCINE AMINOPEPTIDASE

(75) Inventor: Gabriel Pulido-Cejudo, Ottawa (CA)

(73) Assignee: Her Majesty the Queen in right of Canada, as represented by the Minister of Health (CA)

( * ) Notice: Subject to any disclaimer, the term of this patent is extended or adjusted under 35 U.S.C. 154(b) by 0 days.

(21) Appl. No.: 09/538,831

(22) Filed: Mar. 30, 2000

(30) Foreign Application Priority Data

Mar. 30, 1999 (CA) .............................................. 2267481

(51) Int. Cl.$^7$ ............................ C07K 16/40; C12N 5/16

(52) U.S. Cl. .................. 530/388.26; 435/338; 435/326; 530/388.1

(58) Field of Search .......................... 530/388.1, 388.2, 530/388.85, 388.26; 424/138.1, 141.1, 146.1, 156.1, 198.1; 435/70.21, 326, 338, 346

(56) References Cited

U.S. PATENT DOCUMENTS 5,179,008 A * 1/1993 Kahan et al. ............. 435/70.21

OTHER PUBLICATIONS

Pulido–Cejudo, Gabrial, et al, "NDP–Kinase And Leucine Aminopeptidase: Two Prognostic Factors Of Cellular Invasiveness and Metastasis of Human Brain Tumours", Journal of Cellular Biochemistry Supplement, (1994) vol. 0, No. 18D, pp. 111. Meeting Info.: Keystone Symposium On Molecular Basis Of Cancer Therapy Tamarron, Colorado, USA Mar. 4–10, 1994, XP000916389.

Database WPI; Section Ch, Week 198133; Derwent Publications Ltd., London, GB; Class B04, AN 1981–59499D; XP002145124 and JP 56 078600 A (Eiken Kagaku KK), Jun. 27, 1981 (Jun. 27, 1981).

Pulido–Cejudo, Gabriel et al: "Critical Interdependency: From the Role of Estrogen on Breast Cancer to the Susceptibility of Women Towards HIV Infection", NATO Sci. Ser., Ser. A (1999), 311 (Intermolecular Cross–Talk in Tumor Metastasis), 123–136, XP000916826.

Database Chemabs [Online] Chemical Abstracts Service, Columbus, Ohio, US; Niinobe, Michio: "Studies on Leucine Aminopeptidase in Normal and Cancerous Tissues in Man", retrieved from STN, Database accession No. 84:178003, XP002145123.

Weber H: "[Significance of Leucine Aminopeptidase]. Die Bedeutung der Leucin–Aminopeptidase." Deutsche Medizinische Wochenschrift, (Jan. 24, 1969) 94 (4) 181–4., XP000916687, p. 183.

Deng, Jing T. et al: "Purification of Circulating Liver Plasma Membrane Fragments Using A Monoclonal Antileucine Aminopeptidase Antibody", Hepatology (Philadelphia) (1996), 23 (3), 445–54, XP000916789.

PCT International Search Report; PCT Application No. PCT/CA 00/00332; filed Mar. 30, 2000.

Deng J.T. et al; "Purification of Circulating Liver Plasma Membrane Fragments Using A Monoclonal Antileucine Aminopeptidase Antibody"; *Hepatology* 1996 Mar.; 23(3):445–54

Dunzendorfer U. and Drahovsky D.; "Estrogens in Carcinoma of the Prostate: Effects on Enzymes and Nad Polypeptide Hormones"; *Arzneim.–Forsch./Drug Res.* 1978; 28(1), Heft 6:1027–1030.

Gupta S.K. et al: "Serum Leucine Aminopeptidase Estimation: A Sensitive Prognostic Indicator of Invasiveness In Breast Carcinoma"; *Indian J Pathol Microbiol* 1989 Oct.; 32(4):301–5.

Kobayashi H. et al; "[The Significance of Serum Leucine Aminopeptidase (P–LAP) Determination in the Gynecological Malignancies]"; *Nippon Sanka Fujinka Gakkai Zasshi* 1985 May;37(5):696–702.

Kohno H. et al; "Immunoaffinity Purification and Characterization of Leucine Aminopeptidase From Human Liver"; *J Biol Chem* 1986 Aug. 15;261(23):10744–8.

Leyhausen G. et al; "Immunochemical Identification of the Cell Surface Bound Leucine Aminopeptidase,The Target Enzyme for the Immunostimulant Bestatin"; *J Antibiot (Tokyo)* 1983 Jun.;36(6):728–34.

Oettgen H.C. and Taylor A.; "Purification, Preliminary Characterization, and Immunological Comparison of Hog Lens Leucine Aminopeptidase (EC 3.4.11.1) with Hog Kidney and Beef Lens Aminopeptidases"; *Anal Biochem* 1985 Apr.;146(1):238–45.

(List continued on next page.)

Primary Examiner—Anthony C. Caputa
Assistant Examiner—Misook Yu
(74) Attorney, Agent, or Firm—Thompson Hine LLP

(57) ABSTRACT

The identification and characterization of risk factors and their molecular implications in the pathophysiology of human diseases such as cancer is essential for designing efficient diagnostic assays and therapeutic compounds. Estrogenic steroids, under normal physiological conditions, have been shown to play a critical function in several tissues. The response of such a variety of tissues to estrogen stimulation can explain in part its active role in the development and progression of different human diseases, particularly Breast Cancer. Searching for estrogen-responding cellular factors in parental cells of primary human breast carcinomas obtained from tumor biopsies an isoenzyme of putative Leucine Aminopeptidase (LAPase; EC 3.4.11.1) was indenditifed. Results have demonstrated that this marker is found to be elevated in the sera of women with invasive ductal and metastatic carcinomas. A monoclonal antibody against this cellular marker have been produced. This invention refers to the use of LAPase monoclonal antibodies for first line confimatory blood-based testing for Breast Cancer.

2 Claims, 2 Drawing Sheets

OTHER PUBLICATIONS

Partanen S. and Syrjanen K.; "Histochemically Demonstrable Enzyme Activities and Their Independence of the Hormone receptor Content in Female Breast Carnicoma"; *Histopathology*, 1982, 6:771–7.

Prall, O.W.J. et al;"Estrogen–Induced Activation of Cdk4 and Cdk2 $G_1$–S Phase Progression Is Accompanied by Increased Cyclin D1 Expression and Decreased Cyclin–Dependent Kinase Inhibitor Association With Cyclin E–Cdk2"; *J. Biol. Chem.* 1997; 272: pp: 10882–10894.

Pulido–Cejudo Gabriel et al; "Critical Interdependency: From the Role of Estrogen on Breast Cancer to the Susceptibility of Women Towards HIV Infection"; *Intermolecular Cross–Talk in Tumor Metastasis*; Series A: Life Sciencesvol. 311; Skouteris George G. and Nicolson Garth L.; IOS Press, 1999; Washington D.C.. P. 123–136.

Pulido–Cejudo Gabriel et al; "Increase Expression of Leucine Aminopeptidase in Human Breast Carcinoma Cell Lines: A Target for Combined Chemokine Therapy." Abstract presented at the Keystone Symposia on Molecular and Cellular Biology; Feb. 4, 1997; Abstract No. 324, Sec.: Development of Immunotherapies.

Pulido–Cejudo Gabriel et al; "Structural and Functional Homology Between p21 (WAF1) and Leucine Aminopeptidase: A New Insight in the Pathophysiology of Breast Cancer." Abstract presented at the Keystone Symposia on Molecular and Cellular Biology; Feb. 22, 1998; Abstract No. 121, Sec.: Etiology and Pathogeneses of Breast and Prostate Cancer.

Sutherland, R.L. et al; "Hormone and Their Actions" Part 1, van der Molen, H.J., King R.J.B. and Cooke, B.A. eds. *Elsevier Science Publishing B.V.,* Amsterdam. 1998 pp 197–215.

Takao OTA, M.D. et al; "Cystine Aminopeptidase and Leucine Aminopeptidase of Choriocarcinoma Cells Grown in Culture."; *American Journal of Obstetrics and Gynaecology* 1975 Jul. 15;122(6):698–703.

Tsavaris N.B. et al; "Correlation of Histoenzymological Studies with the Response to Chemotherapy and Survival in Breast Cancer Patients."; *Cancer Lett* 1988 Nov.;42(3):225–230.

* cited by examiner

MONOCLONAL ANTIBODY AGAINST ESTROGEN STIMULATED LEUCINE AMINOPEPTIDASE

This application claims benefit of foreign priority from Canada patent application 2,267,481, filed Mar. 30, 1999.

The present invention relates to a monoclonal antibody which demonstrates specific binding to human estrogen-responsive isoenzyme of Leucine Aminopeptidase (es-LAPase). The present invention also relates to the hybridoma cell line, designated as 7B6, and the monoclonal antibody produced by the same. The present invention further relates to a diagnostic system using the monoclonal antibody from the hybridoma cell line 7B6, to detect blood, serum or plasma levels of the estrogen responsive isoenzyme of Leucine Aminopeptidase. The antibody is particularly useful for rapid diagnostic tests for breast cancer.

BACKGROUND OF THE INVENTION

The identification and characterization of risk factors and their molecular implications in the pathophysiology of human diseases such as breast cancer is essential for designing efficient diagnostic assays and therapeutic compounds. Amongst the various risk factors associated with the onset of early events leading to Breast Cancer, estrogen and estrogen-like compounds with estrogenic mimicking activity remain the most important determinants in the early events and progression of breast carcinogenesis. Under normal physiological conditions, there are several tissues whereby estrogenic steroids have been shown to play a critical function. These include the development of the reproductive tract, particularly secondary organs, such as the mammary glands. In addition, estrogens are also involved in the fine regulation of bone growth, liver and cardiovascular function and the estrus cycle, most likely through the induction of cell proliferation in target tissues [Sutherland R. L. et al., pp. 197–215, Elsevier Science Publishing B. V., Amsterdam., Shekhar P. V. M., et al., *J. NatL Cancer. Inst.*, 89: 1774–1782.]. The response of such a variety of tissues to estrogen stimulation can explain in part its active role in the development and progression of different human carcinomas and in particular of Breast Cancer. Although the precise molecular mechanisms by which estrogen stimulation regulates various physiological functions requires further elucidation, this steroid is involved in both "immediate-early" and "early" events of cell function. In this regard, it appears that immediate early events induced by estrogen lead to an increased cellular proliferation most likely through the reduction in the cell cycle by accelerating the rate at which cells progress from the $G_1$ phase towards the S phase. Recently, it has been proposed that estrogen promotes cellular proliferation by co-activating at similar estrogen concentrations, the expression of cyclin D1-Cdk4 and cyclin E-Cdk2, two critical and potentially interrelated $G_1$ regulatory peptides [Prall, O. W. J., et al., *J. Biol. Chem.*, 272: 10882–10894.].

Diagnostic assays are available for breast cancer. For example, imaging techniques such as ultrasounds and x-rays (mammographies) are widely used to detect tumours. These imaging techniques, however, suffer from a limitation in the resolution of the image which prevents the detection of tumours below a certain size.

Histological analysis of biopsies is also a common procedure for the diagnosis of breast cancer and this technique relies on identification of visible phenotypes of the cells. However, this analysis is somewhat subjective and depends on the skill of the examiner.

Molecular diagnostics assays are also available. Among the most widely relied upon is an assay which measures estrogen and progesterone receptors on cells obtained from biopsies. This assay is useful to determine whether a particular type of cancer will be responsive to hormonal therapy.

Flow cytometry can also be used to measure parameters, such as DNA content and the proportion of cells in a particular phase of the cell cycle, that correlates with the presence of cancerous cells.

However, histology, estrogen and progesterone receptor analysis and flow cytometry all require that biopsies be taken and that the sample be extensively processed.

Therefore, there is a need for more rapid and less invasive methods of diagnosing breast cancer. In particular, sensitive assays to detect the presence of cellular markers, preferably in the blood, which reflect the presence of metastasis are desirable. Even more desirable, given the prominent role of estrogen in the progression of breast cancer, are cellular markers, other than estrogen and progesterone receptors, responsive to estrogen.

SUMMARY OF THE INVENTION

The present invention relates to a monoclonal antibody which demonstrates specific binding to human estrogen-stimulated leucine aminopeptidase (es-LAPase). The present invention further relates to a diagnostic system using the monoclonal antibody to detect blood, serum, plasma or tissue levels of the es-LAPase.

Thus, according to the present invention there is provided a monoclonal antibody which is specific for es-LAPase.

In a further embodiment of the present invention there is provided a method of detecting breast cancer in a patient by determining the level of es-LAPase in a sample.

This invention is also directed to a method for detecting a metastatic cancer in a patient by determining the level of es-LAPase in a sample.

BRIEF DESCRIPTION OF THE DRAWINGS

These and other features of the invention will become more apparent from the following description in which reference is made to the appended drawings wherein.

DESCRIPTION OF PREFERRED EMBODIMENT

The present invention relates to a monoclonal antibody which demonstrates specific binding to human estrogen-stimulated leucine aminopeptidase (es-LAPase) either in its soluble or membrane associated form. The present invention further relates to a diagnostic system using the monoclonal antibody to detect blood, serum, plasma or tissue levels of the es-LAPase.

Searching for estrogen-responding cellular factors in parental cells of primary human breast carcinomas obtained from tumour biopsies, the inventor isolated an isoenzyme of the putative leucine aminopeptidase (LAPase; EC 3.4.11.1). This LAPase isoenzyme is released into the extracellular environment upon estradiol incubation of parental epithelial-like cells from human breast carcinomas. Estrogen activation was dose-dependent with an optimal LAPase induced activation at 100 nM.

Figure 1:
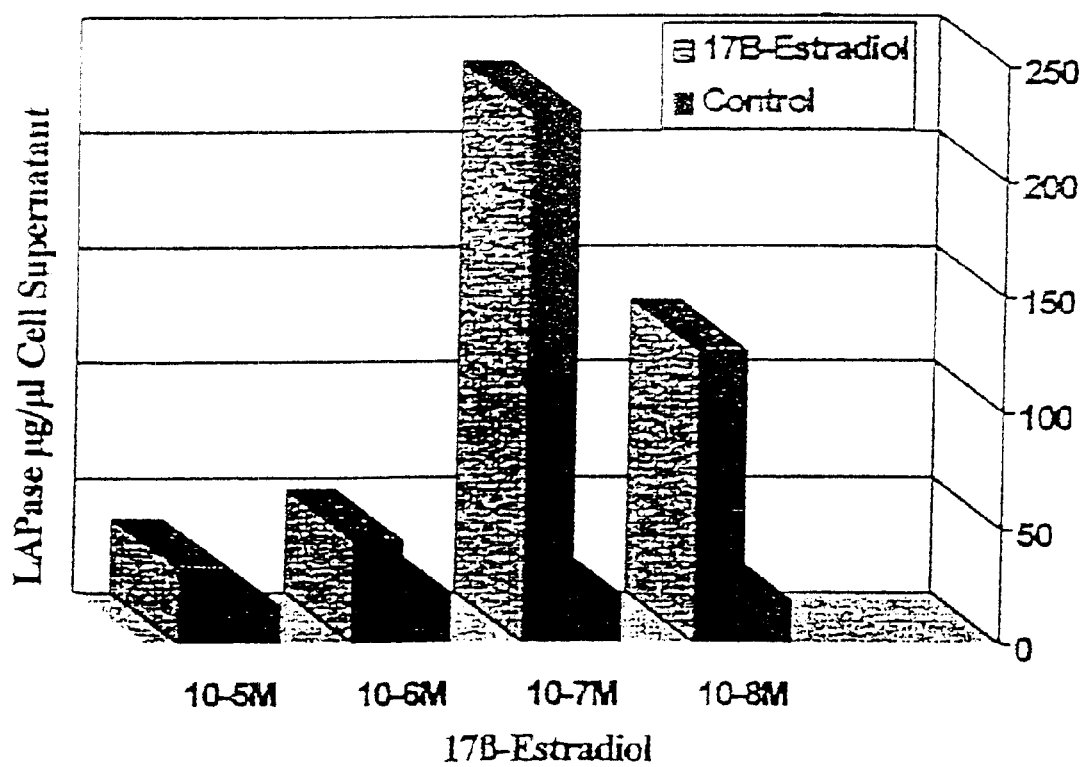
FIG. 1 shows the effect of estrogen on LAPase activity in cell supernatents of primary parental breast cancer cell lines.

To obtain a leucine aminopeptidase isoenzyme responsive to estrogens, epithelial-like cells from human breast carcinoma biopsies were incubated with an estrogen. More preferably with estradiol at concentrations of between $10^{-8}$M and $10^{-5}$ M and preferably at a concentration of $10^{-7}$M. With reference to FIG. 1 it is observed that this incubation promotes the release of es-LAPase. The enzyme was purified from cell supernatents by HPLC-gel permeation followed by DEAE-Cellulose and Bestatin-Sepharose affinity chromatography. The purified es-LAPase exhibits a molecular weight of 315 kDa as estimated by gel permeation on a Bio-Sil™ SEC-250 column (600×7.5 mm) using thyroglobulin (MW 670 kDa); bovine gamma globulin (MW 18 kDa); chiken ovalbumin (MW 44 kDa) and equine myglobin (17 kDa). The isoenzyme of LAPase of the present invention can thus be distinguished from other isoenzymes reported in the literature and which exhibit different molecular weights.

The monoclonal antibody of the present invention was prepared by conventional procedures, generally following the methods of Campbell (Campbell, A. M. (1984). Amsterdam, Elsevier: 219–223.) and Lietzke and Unsicker (Lietzke, R. et al., (1985) *J. Immunol. Methods*, 76:223–228). According to this method, tissue culture adapted mouse myeloma cells are fused to antibody producing cells from immunized mice to obtain hybrid cells that produce large amounts of a single antibody molecule. In general, the antibody producing cells are prepared by immunizing an animal, for example, mouse, rat, rabbit, sheep, horse, or bovine, with an antigen. The immunization schedule and the concentration of the antigen in suspension is such as to provide useful quantities of suitably primed antibody producing cells. These antibody producing cells can be either spleen cells, thymocytes, lymph node cells and/or peripheral blood lymphocytes.

The antibody producing cells are then fused with myeloma cells, cell lines originating from various animals such as mice, rats, rabbits, and humans can be used, using a suitable fusion promoter. Many mouse myeloma cell lines are known and available generally from members of the academic community and various depositories, such as the American Type Culture Collection, Manassas, Va. The myeloma cell line used should preferably be medium sensitive so that unfused myeloma cells will not survive in a selective media, while hybrids will survive. The cell line most commonly used is an 8-azaguanine resistant cell line, which lacks the enzyme hypoxanthine-guanine-phosphoribosyl-transferase and therefore will not be supported by HAT (hypoxanthine-aminopterin-thymidine) medium. In general, the cell line is also preferably a "non-secretor" type, in that it does not produce any antibody. The preferred fusion promoter is polyethyleneglycol having an average molecular weight from about 1000 to about 4000. Other fusion promoters such as polyvinylalcohol, a virus or an electrical field can also be used.

The immortalized cells (hybridoma) must then be screened for those which secrete antibody of the correct specificity. The initial screening is generally carried out using an enzyme-linked immunosorbent assay (ELISA). Specifically, the hybridoma culture supernatants are added to microtitre plates which have been previously coated with the antigen, in this case purified es-LAPase. A bound specific antibody from the culture supernatants can be detected using a labelled second antibody, for example, goat anti-mouse IgG labelled with peroxidase, which is commercially available. Cultures that are positive against es-LAPase antigen are then subjected to cloning by the limiting dilution method. Secondary hybridoma cultures are re-screened as described above. The cultures are then evaluated as to determine whether or not the antibody binds the antigen and to determine the kinetic profile of antigen binding. Selected cultures based on these results are subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the sub-population exhibits the production of a specific antibody, which is indicative of the "stability" of the hybridoma. In addition, hybridoma culture wells often have multiple colonies some of which may be antibody non-producers. The cloning process allows the selection of a positive hybrid which is derived from a single cell.

In one embodiment of the present invention there is provided a monoclonal antibody, which has been designated Mab 7B6. The hybridoma cell line producing this monoclonal antibody has been deposited with the International Depositary Authority of Canada, Room 5190, 1015 Arlington Street, Winnipeg, Manitoba, Canada, R3E 3R2, on Mar. 23, 2000, under Accession Number IDAC 230300-1. This monoclonal antibody is of the IgG1a subtype. It recognizes both the soluble and membrane associated form of es-LAPase. A person of ordinary skill in the art will recognize that other antibodies, both polyclonal and monoclonal can be prepared according to the present invention. In one aspect of this invention, MAb 7B6 can be coupled to a solid matrix. The matrix may be, but is not limited to, a protein G matrix. MAb 7B6 coupled to a matrix may be used to immunoprecipitate es-LAPase. This immunoprecipitation may reduce non-selective binding of the antibody. The immunoprecipitate may be useful to determine the activity of the enzyme or to perform other assays.

The hybridoma cell lines described in the present application have been deposited in accordance with 37 C.F.R. §1.808. Furthermore, subject to paragraph (b) of 37 C.F.R. §1.808, all restrictions imposed by the depositor on the availability to the public of the deposited material will be irrevocably removed upon the granting of any patent issuing from this application or from any continuing application based thereon.

The present invention also encompasses the antibody of the present invention and any fragments thereofcontaining the active binding region of the antibody such as Fab, F(ab)$_2$ and Fv fragments. These fragments can be obtained from the 7B6 antibody by using techniques well known to those of skills in the art (Rousseaux et al. Methods Enzymology, 121:663–69, Academic Press, 1986).

A further embodiment of the present invention encompasses antibodies or fragments thereof capable of binding the same antigenic determinant as the 7B6 antibody.

Including, but not limited to, antibodies possessing the same antigenic specificity as the 7B6 antibody but originating from a different species or having a different isotype or exhibiting different binding affinities. It is envisioned that class and isotype variants of the antibody of the present invention can be prepared using recombinant class switching and fusion techniques that are well known to those skilled in the art (see for example: Thammana et al. Eur. J. Immunol, 13:614, 1983; Oi et al., Biotechnologies, 4(3):214–221, Liu et al. Proc. Nat'l. Acad. Sci. (USA), 84:3439–43, 1987; Neuberger et al., Nature 312:604–608, 1984 and Spira et al. J. Immunol. Meth., 74:307–15, 1984).

The monoclonal antibody of the present invention can be produced either using a bioreactor or from ascites, both procedures of which are well known in the art.

The monoclonal antibody of the present invention can be used in an immunoassay system for determining blood, serum, plasma or tissue levels of es-LAPase.

Current immunoassays utilize a double antibody method for detecting the presence of an analyte. These techniques are reviewed in "Basic Principals of Antigen-Antibody Reaction", Elvin A. Labat, (Methods in Enzymology, 70, 3–70, 1980). Such systems are often referred to as fast format systems because they are adapted to rapid determinations of the presence of an analyte. The system requires high affinity between the antibody and the analyte. According to one embodiment of the present invention, the presence of es-LAPase is determined using a pair of antibodies, each specific for es-LAPase. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting es-LAPase in a sample of biological fluid. In this method, the analyte (es-LAPase) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports were plates, tubes or beads of polystyrene which are well known in the field of radioimmunoassay and enzyme immunoassay. More recently, a number of porous material such as nylon, nitrocellulose, cellulose acetate, glass fibres and other porous polymers have been employed as solid supports.

One embodiment of the present invention uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labelled antibody. The visual detection of the labelled antibody provides an indication of the presence of the target analyte in the sample.

Another example of a flow-through device is disclosed in Kromer et al. (EP-A 0 229 359), which described a reagent delivery system comprising a matrix saturated with a reagent or components thereof dispersed in a water soluble polymer for controlling the dissolution rate of the reagent for delivery to a reaction matrix positioned below the matrix.

In migration type assays, a membrane is impregnated with the reagents needed to perform the assay. An analyte detection zone is provided in which labelled analyte is bound and assay indiciais read. For example, see Tom et al. (U.S. Pat. No. 4,366,241), and Zuk (EP-A 0 143 574). Migration assay devices usually incorporate within them reagents which have been attached to coloured labels thereby permitting visible detection of the assay results without addition of further substances. See for example Bernstein (U.S. Pat. No. 4,770,853), May et al. (WO 88/08534), and Ching et al. (EP-A 0 299 428). The monoclonal antibody of the present invention can be used in all of these known types of flow-through devices.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of coloured labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Other examples of biological diagnostic devices, which can be used for the detection of es-LAPase, using the monoclonal antibody of the present invention, include the devices described by G. Grenner, P. B. Diagnostics Systems, Inc., in U.S. Pat. Nos. 4,906,439 and 4,918,025.

In one embodiment of the present invention, the diagnostic test uses a blood sample tube which is commonly used to draw blood samples from patients. The inside wall of the tube acts as a carrier for the monoclonal or polyclonal antibodies and required reagents or detection means, needed to produce a measurable signal. In this embodiment the capture antibody is immobilized onto the wall of the test tube. After the sample is drawn from the patient, the user simply shakes the sample with the detector antibody in the tube so that the detector antibody reacts with any es-LAPase in the blood. In this example the monoclonal antibody of the present invention can be either the capture antibody or the detector antibody. It may be necessary to use a sample wherein the red blood cells have been removed, so that the red blood cells will not interfere with the analysis of the results. If the analyte is present in the blood, it will be sandwiched between the capture antibody and the detector antibody which contains a suitable label for direct detection or reacts with the reagents in an indirect assay. The solid support (the test tube) can then be rinsed free of unbound labelled material. A variety of solid supports can be used according to this method, for example, test tube walls, plastic cups, beads, plastic balls and cylinders including microtitre plates, paper, and glass fibres.

There are currently available several types of automated assay apparatus which can undertake rapid format assays on a number of samples contemporaneously. These automated assay apparatus include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of work stations each of which performs one of the steps in the test procedure. The assay element may be transported from one work station to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorometer which are included within the assay system.

The automated assay instruments of PB Diagnostic Systems, Inc. are described in U.S. Pat. Nos. 5,051,237; 5,138,868; 5,141,871 and 5,147,609.

A description of the IMX™ Analyzer is included in the "Abbott IMX Automated Bench Top Immunochemistry Analyzer System" by Fiore, M. et al., *Clinical Chemistry*, 35, No. 9, 1988. A further example of these analyzers has been described in U.S. Pat.No. 4,956,148 entitled "Locking Rack and Disposable Sample Cartridge" issued to C. J. Grandone on Sep. 1, 1990, and assigned to Abbott Laboratories, which describes a carousel for carrying a plurality of reaction cells for use in connection with the Abbott IMX™ system. A further development in the art has been described in Canadian Patent Application 2,069,531, Chadwick M. Dunn et al., assigned to Abbott Laboratories wherein the immunochemistry analyzer system, described in this prior art application, has the capability of testing for up to three or four analytes in a single batch during a single run using currently available instrumentation. The system described in the Canadian application referred to above enables the users to group three small batches of assays together rather than run three separate analysis. The monoclonal antibody of the present invention can be used in these automated analyzers.

A further class of immunochemical analyzer systems, in which the monoclonal antibody of the present invention can be used, are the biosensors or optical immunosensor systems. In general an optical biosensor is a device which uses optical principles quantitatively to convert chemical or biochemical concentrations or activities of interest into electrical signals. These systems can be grouped into four major categories: reflection techniques; surface plasmon resonance; fibre optic techniques and integrated optic devices. Reflection techniques include ellipsometry, multiple integral reflection spectroscopy, and fluorescent capillary fill devices. Fibre-optic techniques include evanescent field fluorescence, optical fibre capillary tube, and fibre optic fluorescence sensors. Integrated optic devices include planer evanescent field fluorescence, input grading coupler immunosensor, Mach-Zehnder interferometer, Hartman interferometer and difference interfermoter sensors. These examples of optical immunosensors are described in general in a review article by G. A. Robins (Advances in Biosensors), Vol. 1, pp.229–256, 1991. More specific description of these devices are found for example in U.S. Pat. Nos. 4,810,658; 4,978,503; 5,186,897; R. A. Brady et al. (Phil. Trans. R. Soc. Land. B 316, 143–160, 1987) and G. A. Robinson et al. (in Sensors and Actuators, Elsevier, 1992).

Another immunochemical analyzer is flow cytometry. In flow cytometry the sample containing the antigen is reacted with a fluorescently labelled form of the monoclonal antibody of the present invention. The sample is passed in front of a laser beam of a given wavelength capable of exciting the chromophore on the antibody. Each particle or cell having the antibody bound to it will fluoresce and will be detected. This technique allows the analysis of specific cell types and in particular of specific blood cell types. It is therefore useful for the detection of cells exhibiting the es-LAPase antigen.

In one embodiment of the present invention, es-LAPase is detected in a sample of blood, serum or plasma, using the monoclonal antibody of the present invention, in a device comprising a filter membrane or solid support with a detection section and a capture section. The detector section contains an antibody (a detector antibody), which will react with es-LAPase. The detector antibody is reversibly immobilized onto the solid support and will migrate with the sample, when in use. It is preferred that the detector antibody is labelled, for example with a radionucleotide, an enzyme, a fluorescent moiety, luminescent moiety or a coloured label such as those described in the prior art, and discussed above. The capture section comprises a capture antibody, which is irreversibly immobilized onto the solid support. The antibodies, capture and detector antibody, and the necessary reagents are immobilized onto the solid support using standard art recognized techniques, as disclosed in the flow-through type immunoassay devices discussed previously. In general, the antibodies are absorbed onto the solid supports as a result of hydrophobic interactions between non-polar protein substructures and non-polar support matrix material.

According to this embodiment of the present invention, if es-LAPase is present in the blood, it will react with the detector antibody in the detector section and will migrate on the filter membrane towards the capture section where the analyte will further bind with the capture antibody. Thus, es-LAPase will be sandwiched between the capture antibody and the detector antibody, which contains a suitable label.

In this example of the present invention, if the detector antibody is labelled with a coloured label or an enzyme which will produce a coloured label, the patient's blood would first require centrifugation or some pre-filtering in order to remove the red blood cells so that the colour of the red blood cells will not interfere with the coloured labels. If radioactive labels or flourescent labels are to be used, a pre-filtration or centrifugation step may not be required. In this embodiment, the monoclonal antibody of the present invention can be either the capture antibody or the detector antibody. In one embodiment, the monoclonal antibody of the present invention is a capture antibody. The detector antibody can be other es-LAPase monoclonal antibodies, monoclonal antibodies reactive to other isoforms of LAPase, orpolyclonal anti-es-LAPase antibodies. Either chicken, rabbit, goat or mouse polyclonal antibodies can be used. Many such antibodies are known and can be prepared and labelled by known methods.

This immunoassay system is generally described in U.S. Pat. No. 5,290,678. The antibody of this invention is particularly useful in this system because of its high affinity for es-LAPase.

In a further embodiment of this invention the monoclonal antibody 7B6 can also be used to monitor patients that are at risk of developing breast cancer since serum es-LAPase is affected by estrogens and that estrogens have been identified as important factors in the progression of certain types of breast cancer. Individual at risk may include those taking estrogen based birth control pills, hormonal replacement therapy or individuals having abnormal hormonal patterns.

As would be recognized by one of skill in the art, the above described embodiments of this invention may have to be modified to distinguish between the soluble and membrane associated form of es-LAPase.

As would also berecognized by one of skill in the art, a base line level of es-LAPase may be present in normal patients. Thus, in the present invention, in certain embodiments, the levels of es-LAPase above normal will be determined. This can be accomplished by either comparing the results to the results of a normal patient, or adjusting the sensitivity of the immunoassay so that only values above a certain threshold will show as a positive result.

As will be clearly indicated in the examples infra, es-LAPase levels are correlated with breast cancer and the presence of metastasis in patients with breast cancer. Thus, the monoclonal antibody 7B6 of the present invention, along with the embodiments described supra is particularly useful as a new diagnostic tool.

In order that the invention described herein may be more fully understood, the following examples are set forth. It should be understood that these examples are for illustrative purposes only and are not to be construed as limiting the scope of this invention in any manner.

EXAMPLES

Example 1

Isolation and Purification of Estradiol-Dependent Leucine Aminopeptidase (LAPase)

Primary parental breast carcinoma cells obtained from human tumour biopsies were stimulated with 100 nM 17-β-Estradiol for 24 hours or cell media alone as a control. The cell media was RPMI 1640 medium+10% FCS+100U/ml Penicillin+100 μg/ml Streptomycin. Cell supernatants were collected then after and dialyzed against PBS in seamless cellulose tubing (MW 12,400) for 12 hours at 4° C. LAP was subsequently purified from the dialyzed cell supernatants using HPLC-gel permeation followed by DEAE-Cellulose and Bestatin-Sepharose affinity Chromatography. Briefly, the cell supernatant was applied to a Bio-Sil SEC-250 column (600×7.5 mm) previously equilibrated in a buffer containing 100 mM Sodium Phosphate buffer pH 6.8, 100 mM $Na_2SO_4$, 1 μM $ZnCl_2$ and 10% glycerol. The column was washed with 300 ml of the same buffer at a flow rate of 0.5 ml/min. Protein was concentrated to 10 ml by ultrafiltration using YM5 membrane (5000 M. W. cutoff, Amicon Div., Danvers, Mass., USA). The concentrate was applied to a DEAE cellulose column (2.6 cm×28.5 cm) equilibrated and washed with 50 mM Tris-HCl buffer pH 7.5; 1 μM $ZnCl_2$; and 10% (v/v) glycerol. es-LAPase was eluted using a linear gradient (0 to 1 M NaCl in Tris buffer) at a flow rate of 0.50 ml/min. A Bestatin-affinity column was prepared using Ultralink EDC/DADPA Amide bonding matrix (Pierce, Rockford, Ill. U.S.A.) by reacting 100 mg of pure Bestatin with the carbodiimide EDC/DADPA matrix following the procedure provided by the manufacturer. Prior to loading the es-LAPase containing eluent, the Bestatin-affinity column was equilibrated with 10 mM Tris-HCl pH 8.0 containing 1 μM $ZnCl_2$ and washed with 300 ml of this binding buffer. es-LAPase was recirculated through the system using a peristaltic pump at a flow rate of 0.10 ml/min, for 2 hours. Following this recirculation, the column was washed with eight column volumes of binding buffer. Bestatin-bound es-LAPase was eluted with a linear gradient (0–0.5 M NaCl) prepared in binding buffer 10 mM Tris-HCl pH 8.0 containing 1 μM $ZnCl_2$. Elution of bound es-LAPase was monitored by absorbance at 280 nm. Purified es-LAPase fractions were aliquoted in 500 μl and stored until further use in 50 mM Tris-HCl pH 7.8 and 50 μM $ZnCl_2$. es-LAPase protein concentration following each purification step was determined as described by Pulido-Cejudo [J. Chromatogr. B 660 (1994) 37–47)]. Briefly, samples (100–200 μl) were dialysed against deionized water and 2–20 μl of each were placed in polypropylene tubes. Samples were dried for 60 min at 110° C. for 90 min and subsequently neutralized with 250 μl of glacial acetic acid. The samples were then reacted with 500 μl of the following ninhydrin-hydrindantin solution: 2 g of ninhydrin and 150 mg of hydrindantin (Sigma) were dissolved in 65 ml of 2-methoxyethanol and then 35 ml of 4 M sodium acetate (pH 5.5) were added. The tubes were incubated at 110° C. for 15 min. Before reading the absorbance of the samples at 570 nm, 2.5 ml of 5% (v/v) ethanol were added. Protein content was determined by interpolation on an absorbance curve obtained with samples of BSA (1–10 μg). A summary of the purification fold of the 17-β-Estradiol-stimulated LAPase from parental cells of human breast carcinomas is set out in Table 1.

TABLE 1

Summary of Purification of LAP from Human Breast Carcinoma Parental Cells

| Step | Protein[1] (mg) | Total Activity[2] (nmole/min) | Specific Activity[2] (nmole/min/mg) | Fold | Yield % |
|---|---|---|---|---|---|
| Supernatant | 15.4 | 98.21 | 6.37 | 1 | 100 |
| Gel Permeation | 4.2 | 82.13 | 19.55 | 3.07 | 83.63 |
| Cellulose DEAE | 0.72 | 48.25 | 67.01 | 10.51 | 49.13 |
| Bestatin-Sepharose | 0.005 | 37.11 | 7422 | 1165 | 37.79 |

[1]the amount of protein was determined after alkaline hydrolysis and quantitative ninhydrin detection of hydrolyzed material as described by Pulido-Cejudo et al. [J. Chromatogr. B 660 (1994) 37–47)].
[2]determined fluorometrically using leucine-β-naphtylamide as a subtrate as described by [Kuramochi, H., et al. (1987) J. Antibiot., 40, 1605–1611].

Example 2

A) Monoclonal Antibody Production and Purification

In producing the hybridoma cell line 7B6 secreting the mouse monoclonal antibody to 17-β-Estradiol-stimulated LAPase, protocols for antigen preparation for immunization, preparation of spleen cells from immune animals, fusion of spleen cells with myeloma cells and plating of fused cells in selective medium was conducted following detailed guidelines described by Campbell [Burdon RH, Knippenberg PHV (eds): Laboratory Techniques in Biochemistry and Molecular Biology, Amsterdam, Elsevier, p219 (1984)] and by Lietzke and Unsicker [Leitzke R. Unsicker K: A Statistical Approach to Determine Monoclonality After Limiting Cell Plating of a Hybridoma Clone, J Immunol Methods 76:223 (1985)].

Briefly, the primary immunization was performed with purified es-LAPase following desalting. Boosts with purified es-LAPase were performed at days 14, 35 & 56. BALB/c mice were screened at days 24 & 45. The mice were sacrificed at day 59 and the splenocytes from the best responder were fused with myeloma cells. Screening was performed by dot blot immunostaining on nitrocellulose.

The hybridoma clone 7B6 was obtained by single cell cloning by limiting dilution. Four dilution tubes in series containing hybridoma cells with medium supplement with 20% FBS+2X OPI were prepared. 100 μl of each dilution was plated in a 96-well plate with 50 μl of splenocyte feeder cells in each well and placed inside a 37° C. 5% $CO_2$ incubator. At day 7, supernatants from each well were removed and screened by dot blot immunostaining on nitrocellulose.

B) Expansion of Hybridoma Clone 7B6

Hybridoma clone 7B6 cells were transferred from the 96 well plate to 0.5 ml medium supplemented with 20% FBS+ 1X OPI+1X HAT in a 24 well plate. Once the cells were dense, they were transferred into 5 mls in a 60 mm dish and then transferred to 10 mls in a 100 mm dish. Once in the 60 mm dish, the cells were weened off hypoxanthine, thymidine and aminopterin. 7B6 hybridoma cells were continued to be grown until in a log phase of growth. Anti-es-LAPase, Mab 7B6 was isolated from collected hybridoma 7B6 cell supernatant by affinity chromatography using Immunopure IgG as per described by manufacturer. Screening was performed by dot blot immunostaining on nitrocellulose.

C) Immunotyping of Mab 7B6

The isotype of Mab 7B6 was determined using Sigma's Immunotype Kit. Briefly, the assay involves binding of Mab 7B6 to a precoated isotyping nitrocellulose membrane strip followed by immunodetection using a sensitive biotin-avidin-enzyme detection system. The immunoglobulin isotype is revealed by self description.

D) Immobilization of Mab 7B6 to Protein G matrix

Following purification of the Mab 7B6, the corresponding IgG1a isotype was subsequently immobilized to a DSS cross-linking system obtained from Pierce (Rockford, Ill., U.S.A) according to the procedures described by the manufacturer. Mab 7 B6 Protein G matrices were used to selectively immunoprecipitate LAPase activity from plasma or cell membrane-bound fractions prior to determining LAPase actvity.

Example 3

ELISA Analysis of Human Breast Carcinoma Parental Cell Line

ELISA analysis of human breast carcinoma parental cell lines was conducted to demonstrate the reactivity of Mab 7B6 against human LAP. Briefly, 50000 parental cells were plated per well in a 96 well plate in RPMI 1640 medium+ 10% FCS+100 U/ml Penicillin+100 μg/ml Streptomycin. The plated cells were cultivated at 37° C. 5% $CO_2$ for 24 hours. The cell supernatants were removed, the cells were washed with PBS and subsequently fixed with 1% gluteraldehyde in PBS for 1 hour at room temperature. Washing with PBS occurred prior to blocking with casein for 1 hour at 37° C. 5% $CO_2$. Following another wash with PBS, serial dilutions of Mab 7B6 were added to the wells and allowed to incubate for 2 hours at 37° C. 5% $CO_2$. Demonstration of the reactivity of Mab 7B6 was evident upon the addition of a secondary antibody, anti-(IgG+IgM) peroxidase conjugated goat anti-mouse IgG+IgM (H+L) followed by the substate, OPD. A summary of the readings taken at 490 nm are set out in Table 2.

TABLE 2

Summary of Reactivity of Mab 7B6 against LAP from Human Breast Carcinoma Parental Cells

| Mab 7B6 (ng/well) | Cell Line 1 OD 490 nm − Blank OD 490 nm | Cell Line 2 OD490 nm − Blank OD 490 nm |
| --- | --- | --- |
| 200 | 0.707 − 0.054 = 0.653 | 0.6 − 0.005 = 0.595 |
| 100 | 0.57 − 0.021 = 0.549 | 0.446 − 0.003 = 0.443 |
| 50 | 0.489 − 0.042 = 0.447 | 0.327 − 0.003 = 0.324 |
| 25 | 0.38 − 0.047 = 0.333 | 0.24 − 0 = 0.24 |
| 12.5 | 0.294 − 0.05 = 0.244 | 0.165 − 0 = 0.165 |
| 6.25 | 0.226 − 0.05 = 0.176 | 0.1 − 0.003 = 0.097 |
| 3.25 | 0.155 − 0.044 = 0.111 | 0.068 − 0.003 = 0.065 |
| 1.56 | 0.107 − 0.05 = 0.057 | 0.043 − 0.002 = 0.041 |
| 0.78 | 0.094 − 0.055 = 0.039 | 0.023 − 0.001 = 0.022 |
| 0.39 | 0.067 − 0.073 = 0 | 0.015 − 0 = 0.015 |
| 0.2 | 0.061 − 0.052 = 0.009 | 0.008 − 0 = 0.008 |
| 0.1 | 0.053 − 0.046 = 0.007 | 0 − 0 = 0 |

Example 4

LAPase Levels in Cell Supernatants Following Estrogen Stimulation

Primary parental breast carcinoma cells were incubated with 100 nM 17-β-Estradiol for 24 hrs and cell media alone as a control. LAPase in supernatants was isolated using MAb 7B6 $_{(IgG1a)}$-protein G-LAPase beads prepared by covalently cross-linking the monoclonal antibody. LAPase activity of the LAPase-immunoprecipitated supernatants was determined fluorometrically using leucine-β-naphthylarnide as the substrate as described by Kuramnochi et al. [Kurarnochi, H. et al., (1987) J. Antibiot., 40:1605–1611].

Purified preparations of the enzyme obtained from Sigma were incubated with 100 nM 17-β-Estradiol for 24 hrs. LAPase activity was determined fluorometrically using leucine-β-naphthylamide as the substrate as described by Kuramochi et al. [Kuramochi, H. et al., (1987) J. Antibiot., 40:1605–1611].

Following estrogen stimulation, maximum release of LAPase was observed at an estrogen concentration of 100 nM following 24 hours of incubation (see FIG. 1). During the same period, LAPase in cell supernatants of control cells remain unchanged. In addition, LAPase activity was determined in supernatants of primary parental cell lines immunoprecipitated with MAb 7B6 $_{(IgG1a)}$-protein-G-LAPase matrix bound antibodies. These results show that the extracellular LAPase activity of estrogen stimulated cells (100 nM) was $7.7 \times 10^{-5}$ U/ml in comparison to $6.4 \times 10^{-6}$ U/ml detected in the supernatant of parental cells incubated for 24 hours with cell media alone as control. In addition, there was no effect of estrogen incubation on LAPase activity in purified preparations of this enzyme alone. Collectively, these results suggest that estrogen effect in LAPase activity encompasses a cellular mediated process.

Example 5

Estrogen-responsive LAPase in Women With Breast Cancer

Mab 7B6 binding to parental cells detected by immunoflowcytometry can be used to detect circulating epithelial like-cells in women with Brest Cancer. In addition, plasma immunoprecipitates using Mab 7B6 consistently show higher levels of LAPase in women with non-invasive ductal and metastatic carcinomas when compared to plasma levels from otherwise healthy women.

A) LAPase Actvity in Plasma of Women With Primary Breast Cancer

LAPase activity in plasma of relapsed patients with primary Breast Cancer compared to aged matched controls of otherwise healthy women, were determined fluorometrically using leucine-β-naphthylamide as the substrate as described by Kuramochi et al. The reaction was stopped by boiling the samples at 100° C. for 10 mins, followed by centrifugation at 780×g at 4° C. for 10 mins. Values obtained represent the average of LAPase activity determined in triplicate in 16 patients from each test group.

LAPase activity was determined using palsma immunoprecipitates obtained by immunoprecipitation using Covalent Mab $7B6_{(IgG1a)}$-Protein-G-LAPase matrices. Briefly, Plasma was spun at 500×g for 10 min. at 4° C. Plasma was removed by aspiration and spun once more at 500×g for 5 min. at 4° C. The resulting plasma was diluted 1:10 with PBS and 800 μl of plasma dilution was added to Mab $7B6_{(IgG1a)}$-G-LAPase beads containing 5 μg of antibody in 200 ul of beads pre-incubated with blocking buffer [50 mM Tris-HCl; 0.5%non-fat dry milk(NFDM)]. Samples were incubated at room temperature (~22° C.) for 15 min with constant gentle rotation in 0.5% BSA pre-coated Eppendorf tubes. After incubation samples were spun at 250×g Eppendorf-Microfuge at room temperature supernatants removed. The beads containing the LAPase activity was washed trice with PBS;0.5% NFDM and finally resuspended in Calcium-free Hank's solution making up a 600 μl final reaction volume and 182 μM 1-leucine-β-naphthylamide. A corresponding blank without LAPase- Covalent Mab 7B6$_{(IgG1a)}$-beads coated with 0.5% NFDM was used as baseline.

Using selective immunoprecipitation of plasma incubated with anti-LAPase Mab-Protein G matix, it was found that LAPase activity in the plasma of women with metastatic disease was four orders of magnitude higher than the control population. Such increase in LAPase activity was less predominant in patients with ductal carcinoma in-situ (DCIS). A summary the results is provided below in Table 3.

TABLE 3

LAPase activity levels in plasma of women with Breast Cancer

| Patient Population (n = 10 per group) | LAPase Activity (U/ml) |
|---|---|
| Normal | 6.16 × 10$^{-4}$ ± 0.82 × 10$^{-4}$ |
| DCIS (non-invasive) | 3.06 × 10$^{-1}$ ± 0.80 × 10$^{-1}$ |
| Metastatic (Lung/Brain) | 1.73 ± 0.08 |

One unit of LAPase is defined as the amount of enzyme required to hydrolyze 1 μmol of L-leucine-β-naphthylamide per min at pH 7.5 and 37° C.

B) Flow Cytometric Detection of Epithelial-Like Breast Carcinoma Cells

Indirect immunofluorescence staining of epithelial-like cells from tumour biopsies was performed by incubating adherent cells with human serum pre-adsorbed Mab 7B6 antibodies. Briefly, confluent cells were washed trice with PBS and incubated at 37° C. with 20 μl of Mab 7B6 antibodies (200 μg/ml) or control mouse IgG1 in a final volume of 2 ml. After 20 min. incubation cells were washed trice once more with PBS and incubated with mouse anti-IgG-PE or mouse anti-IgG-FITC conjugtes for 15 minutes.

Cells were subsequently washed three times with PBS, partially trypsinized and analyzed in a flowcytometer equipped with an air-cooled argon ion laser operating at 10 mwatt. Simultaneous excitation of FITC and PE conjugates was achieved by setting the excitation wavelength at 488 nm.

As shown in Table 4, Mab 7B6 can be used to detect membrane-bound LAPase in parental epithelial-like cells isolated from human breast carcinomas. Screening of LAPase reactivity in circulating cells was examined in normal women and compared to those with ductal carcinoma in situ and with metastatic Breast Carcinomas. Briefly whole blood was spun and buffy-coat removed. Cells within the buffy-coat were washed trice with PBS and incubated with Mab 7B6 [20 μl of Mab 7B6 antibodies (200 μg/ml) or control mouse IgG1] in a final volume of 2 ml of PBS;0.5% NFDM. The % of Mab 7B6 cells in this fraction was subsequently estimated by flowcytometry.

TABLE 4

Membrane-bound LAPase in parental epithelial-like cells isolated from Human Breast Carcinomas

| Patient Population (n = 100 per group) | % Mab 7B6 Positive cells |
|---|---|
| Normal | 0.1–0.5 |
| DCIS (non-invasive) | 5–14 |
| Metastatic (Lung/Brain) | 18–25 |

C) LAPase Levels in Plasma of Women With Primary Breast Cancer

LAPase levels in plasma of women with primary Breast Cancer compared to aged-matched controls of otherwise healthy women, were determined by ELISA using the monoclonal antibody Mab 7B6.

Plasma immunoprecipitates using Mab 7B6 consistently show higher levels of LAPase in women with non-invasive ductal and metastatic carcinomas when compared to plasma levels from otherwise healthy women. A summary of results obtained is set out in Table 5.

TABLE 5

LAPase levels in plasma of women with Breast Cancer

| Patient Population (n = 100 per group) | LAPase Levels (μg/ml) |
|---|---|
| Normal | 5–10 |
| DCIS (non-invasive) | 450–600 |
| Metastatic (Lung/Brain) | 1200–3700 |

All cited references and Patents or Patent Applications are incorporated herein by reference.

The present invention has been defined in terms of certain examples, which are not to be construed as limiting. The full scope of the present invention is defined in the following claims.

Example 6

Inhibitors of es-LAPase

Human Thioredoxin was purified from CD$_4$+T MP6 cells as described by Rosen et al. [Rosen, A. et al. (1995) Int. Immunol. 7, 625–633] and compared to purified Thioredoxin activity from E.Coli. purchased from SIGMA-ALDRICH Canada (Oakville, Ontario Canada).

Thioredoxin was covalently linked through an amide bond to Ultralink EDC/DADPA bonding matrix (Pierce, Rockford, Ill. U.S.A.) by reacting 5 mg of purified Thioredoxin with the carbodiimide EDC/DADPA matrix following the procedure provided by the manufacturer.

Measurements of LAPase were performed spectrophotometrically at 330 nm to measure product formation of β-naphthylamine, using 182 μM 1-leucine-β-naphthylamide as the substrate. The kinetic assays were performed using a Spectronic Genesys 5 spectrophotometer from Milton Roy (Rochester, N.Y.). Absorbance was recorded every sixty seconds, over a period of 30 min. Enzyme kinetic assays were performed using $8.0 \times 10^{-2}$ U of es-LAPase in a final reaction volume of 600 μl and triplicate samples. The reaction mixture contained the following materials added in order and all kept on ice prior to use: es-LAPase, Calcium-free Hank's solution making up a 600 μl final reaction volume and 182 μM 1-leucine-β-naphthylamide. A corresponding blank without es-LAPase was used as baseline. Both of the cuvettes were transferred to the spectrophotometer where the 1-leucine-β-naphthylmide solution was added last, marking time zero of the reaction. The inhibition studies were carried out in the presence of 167 μM Bestatin, 167 μM reduced Gluthathione and 17 μM reduced thioredoxin.

Figure 2:
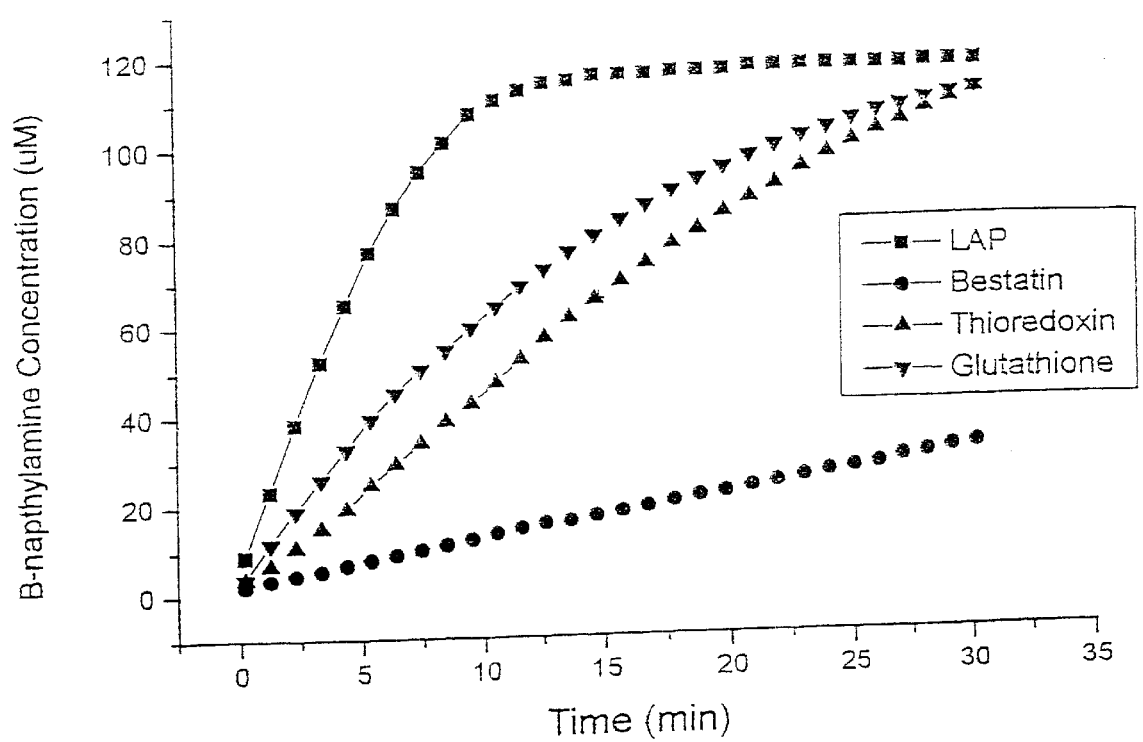
FIG. 2 shows the kinetics of inhibition of LAPase by Bestatin, thioredoxin and glutathione.

FIG. 2 shows the inhibitory effect of both Bestatin and two thiol-containing peptides, reduced thioredoxin and reduced glutathione respectively. Es-LAPase showed significant slower rates of reaction both in the presence of thioredoxin and glutathione in comparison to that observed in the control es-LAPase. In addition, es-LAPase reaction rates were slower in the presence of 17 μM thioredoxin when compared to those observed in samples incubated with 167 μM reduced Gluthathione. In addition, 167 μM Bestatin clearly inhibits es-LAPase activity. As shown in Table 6, reduced thioredoxin is an effective inhibitor of es-LAPase activity. The analysis of the maximum reaction rates (Vmax), Michaelis-Menten (Km) constants and the inhibition constants (Ki) for each inhibitor as presented in Table 6 reveals significant differences in the inhibitory properties of each peptide. In this regard, es-LAPase incubated with Bestatin shows a Vmax value very similar to that observed to es-LAPase alone and a significantly higher Km value. This data confirms the competitive nature of es-LAPase inhibition by Bestatin. In contrast, es-LAPase incubated with reduced thioredoxin leads to a significantly lower Vmax and Km with an intermediate Ki value when compared to those obtained for Bestatin and glutathione. Collectively these data strongly suggest that reduce thioredoxin inhibits es-LAPase in an uncompetitive fashion while with reduced glutahthione es-LAPase inhibition is noncompetitive.

TABLE 6

Bestatin, reduced thioredoxin and glutathione es-LAPase inhibition Constants

|  | Vmax ($10^{-6}$ M/min) | Km ($10^{-4}$ M) | Ki ($10^{-6}$ M) |
|---|---|---|---|
| LAPase alone | 36.8 ± 1.9 | 1.67 ± 0.14 | N/A |
| Bestatin 167 μM | 34.0 ± 3.9 | 48.7 ± 8.4 | 6.22 ± 1.61 |
| Thioredoxin 17 μM | 5.31 ± 0.02 | 0.234 ± 0.006 | 3.40 ± 0.58 |
| Glutathione 167 μM | 17.2 ± 1.5 | 1.78 ± 0.25 | 1.53 ± 0.40 |

The embodiments of the invention in which an exclusive property of privilege is claimed are defined as follows:

1. A monoclonal antibody specific for soluble and membrane associated human estrogen-stimulated leucine aminopeptidase (es-LAPase), produced by hybridoma cell line 7B6, deposited with the International Depository Authority of Canada under Accession number IDAC 230300-1.

2. A hybridoma cell line which produces a monoclonal antibody specific for soluble and membrane associated human estrogen-stimulated leucine aminopeptidase (es-LAPase), as deposited with the International Depository Authority of Canada under Accession number IDAC 230300-1.

* * * * *